United States Patent
Guaneri et al.

(10) Patent No.: US 11,265,234 B2
(45) Date of Patent: Mar. 1, 2022

(54) SYSTEM AND METHOD FOR TRANSMITTING DATA AND ORDERING ASYNCHRONOUS DATA

(71) Applicant: ROM TECHNOLOGIES, INC., Brookfield, CT (US)

(72) Inventors: Joseph Guaneri, Merrick, NY (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Steven Mason, Las Vegas, NV (US); Jonathan Greene, Denver, CO (US)

(73) Assignee: ROM TECHNOLOGIES, INC., Brookfield, CT (US)

( * ) Notice: Subject to any disclaimer, the term of this patent is extended or adjusted under 35 U.S.C. 154(b) by 0 days.

(21) Appl. No.: 17/149,457

(22) Filed: Jan. 14, 2021

(65) Prior Publication Data

US 2021/0144074 A1 May 13, 2021

Related U.S. Application Data

(63) Continuation-in-part of application No. 17/021,895, filed on Sep. 15, 2020, now Pat. No. 11,071,597.
(Continued)

(51) Int. Cl.
*G16H 20/00* (2018.01)
*H04L 43/06* (2022.01)
(Continued)

(52) U.S. Cl.
CPC ............ *H04L 43/06* (2013.01); *G16H 10/60* (2018.01); *G16H 20/00* (2018.01); *H04L 49/552* (2013.01); *H04L 69/22* (2013.01)

(58) Field of Classification Search
CPC ....... H04L 43/06; H04L 49/552; H04L 69/22; H04L 67/12; G16H 10/60; G16H 20/00;
(Continued)

(56) References Cited

U.S. PATENT DOCUMENTS 6,182,029 B1   1/2001  Friedman
6,413,190 B1   7/2002  Wood et al.
(Continued)

FOREIGN PATENT DOCUMENTS

CA   2698078 A1   9/2011
CN   10348880 A   1/2014
(Continued)

OTHER PUBLICATIONS

International Search Report and Written Opinion for International Application No. PCT/US2021/032807, dated Sep. 6, 2021, 11 pages.

*Primary Examiner* — George Manuel
(74) *Attorney, Agent, or Firm* — Dickinson Wright, PLLC; Stephen A. Mason; Jonathan H. Harder

(57) ABSTRACT

A computer-implemented system includes an electromechanical device configured to be manipulated by a patient while performing an exercise session, and a processor in communication with the electromechanical device. The processor is configured to receive data, generate a map packet, and transmit the map packet. The processor is configured to use the data to generate continuity packets, where each of the continuity packets includes a contiguous portion of the data, and transmit the continuity packets. The processor is configured to use the map packet and the continuity packets to cause an output file to be generated.

19 Claims, 7 Drawing Sheets

Related U.S. Application Data

(60) Provisional application No. 63/028,399, filed on May 21, 2020, provisional application No. 62/910,232, filed on Oct. 3, 2019.

(51) Int. Cl.
  *H04L 69/22* (2022.01)
  *G16H 10/60* (2018.01)
  *H04L 49/552* (2022.01)

(58) Field of Classification Search
  CPC .............. G16H 40/67; A61B 2034/105; A61B 2034/258; A61B 34/10; A61B 34/25
  See application file for complete search history.

(56) References Cited

U.S. PATENT DOCUMENTS

| | | |
|---|---|---|
| 6,491,649 B1 | 12/2002 | Ombrellaro |
| 6,890,312 B1 | 5/2005 | Priester et al. |
| 7,169,085 B1 | 1/2007 | Killin et al. |
| 7,209,886 B2 | 4/2007 | Kimmel |
| 7,974,689 B2 | 7/2011 | Volpe et al. |
| 8,751,264 B2 | 6/2014 | Beraja et al. |
| 8,823,448 B1 | 9/2014 | Shen |
| 9,311,789 B1 | 4/2016 | Gwin |
| 9,579,056 B2 | 2/2017 | Rosenbek et al. |
| 9,939,784 B1 | 4/2018 | Berardinelli |
| 10,074,148 B2 | 9/2018 | Cashman et al. |
| 10,130,298 B2 | 11/2018 | Mokaya et al. |
| 10,424,033 B2 | 9/2019 | Romeo |
| 2003/0036683 A1 | 2/2003 | Kehr et al. |
| 2006/0064329 A1 | 3/2006 | Abolfathi et al. |
| 2008/0021834 A1 | 1/2008 | Holla et al. |
| 2009/0011907 A1 | 1/2009 | Radow et al. |
| 2009/0070138 A1 | 3/2009 | Langheier et al. |
| 2010/0248899 A1 | 9/2010 | Bedell et al. |
| 2010/0268304 A1 | 10/2010 | Matos |
| 2011/0172059 A1 | 7/2011 | Watterson et al. |
| 2011/0218814 A1 | 9/2011 | Coats |
| 2012/0065987 A1 | 3/2012 | Farooq et al. |
| 2012/0190502 A1 | 7/2012 | Paulus et al. |
| 2012/0307842 A1* | 12/2012 | Petrov ................ H04N 21/2389 370/474 |
| 2012/0310667 A1 | 12/2012 | Altman et al. |
| 2013/0123667 A1 | 5/2013 | Komatireddy et al. |
| 2013/0296987 A1 | 11/2013 | Rogers et al. |
| 2014/0006042 A1 | 1/2014 | Keefe et al. |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0207264 A1 | 7/2014 | Quy |
| 2014/0257837 A1 | 9/2014 | Walker et al. |
| 2014/0322686 A1 | 10/2014 | Kang |
| 2015/0088544 A1 | 3/2015 | Goldberg |
| 2015/0158549 A1 | 6/2015 | Gros et al. |
| 2015/0161331 A1 | 6/2015 | Oleynik |
| 2015/0339442 A1 | 11/2015 | Oleynik |
| 2015/0341812 A1* | 11/2015 | Dion ................ H04N 21/2404 370/252 |
| 2016/0117471 A1 | 4/2016 | Belt et al. |
| 2016/0140319 A1 | 5/2016 | Stark et al. |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2017/0004260 A1 | 1/2017 | Moturu et al. |
| 2017/0143261 A1 | 5/2017 | Wiedenhoefer et al. |
| 2017/0147789 A1 | 5/2017 | Wiedenhoefer et al. |
| 2017/0181698 A1 | 6/2017 | Wiedenhoefer et al. |
| 2017/0209766 A1 | 7/2017 | Riley et al. |
| 2017/0243028 A1 | 8/2017 | LaFever et al. |
| 2017/0278209 A1 | 9/2017 | Olsen et al. |
| 2017/0300654 A1 | 10/2017 | Stein et al. |
| 2017/0329917 A1 | 11/2017 | McRaith et al. |
| 2017/0344726 A1 | 11/2017 | Duffy et al. |
| 2017/0360586 A1 | 12/2017 | Dempers et al. |
| 2018/0052962 A1 | 2/2018 | Van Der Koijk et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0102190 A1 | 4/2018 | Hogue et al. |
| 2018/0220935 A1 | 8/2018 | Tadano et al. |
| 2018/0240552 A1 | 8/2018 | Tuyl et al. |
| 2018/0263530 A1 | 9/2018 | Jung |
| 2018/0271432 A1 | 9/2018 | Auchinleck et al. |
| 2018/0280784 A1 | 10/2018 | Romeo et al. |
| 2018/0330058 A1 | 11/2018 | Bates |
| 2018/0330824 A1 | 11/2018 | Athey et al. |
| 2018/0373844 A1 | 12/2018 | Ferrandez-Escamez et al. |
| 2019/0019578 A1 | 1/2019 | Vaccaro |
| 2019/0065970 A1 | 2/2019 | Bonutti et al. |
| 2019/0066832 A1 | 2/2019 | Kang et al. |
| 2019/0088356 A1 | 3/2019 | Oliver et al. |
| 2019/0167988 A1 | 6/2019 | Shahriari et al. |
| 2020/0143922 A1 | 5/2020 | Chekroud et al. |
| 2020/0151595 A1 | 5/2020 | Jayalath et al. |
| 2020/0289889 A1 | 9/2020 | Hacking et al. |
| 2020/0401224 A1 | 12/2020 | Cotton |

FOREIGN PATENT DOCUMENTS

| | | |
|---|---|---|
| CN | 104335211 A | 2/2015 |
| CN | 105894088 A | 8/2016 |
| CN | 105930668 A | 9/2016 |
| CN | 106127646 A | 11/2016 |
| CN | 107430641 A | 12/2017 |
| CN | 112603295 A | 4/2021 |
| KR | 20020009724 A | 2/2002 |
| KR | 20160093990 A | 8/2016 |
| KR | 20170038837 A | 4/2017 |
| KR | 20190011885 A | 2/2019 |
| KR | 101988167 B1 | 6/2019 |
| WO | 2019204876 A1 | 10/2019 |

* cited by examiner

SYSTEM AND METHOD FOR TRANSMITTING DATA AND ORDERING ASYNCHRONOUS DATA

CROSS-REFERENCES TO RELATED APPLICATIONS

This application is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. This application also claims priority to and the benefit of U.S. Provisional Patent Application Ser. No. 63/028,399, filed May 21, 2020, titled "System and Method for Transmitting Data and Ordering Asynchronous Data," the entire disclosure of which is hereby incorporated by reference for all purposes.

TECHNICAL FIELD

This disclosure relates generally to systems and methods of transmitting and processing data.

BACKGROUND

Medical devices may include one or more sensors that detect events and generate data pertaining to the events. The data from the sensors may flow in a data stream from the device to a network and, optionally, back to the device. This process can generate exceedingly large amounts of data, requiring substantial memory to use and to store the data. The data may be input into an electronic medical record (EMR) system. EMRs can include information related to the health of a patient, and such information may be contained in or called an "electronic health record." The EMR can use and store electronic health records of patients (e.g., a collection of patient and population health information in a digital format). The health information may be used by a variety of entities, such as health care providers (e.g., physicians, physical therapists, nurses, etc.); insurance companies; billing companies; hospitals; laboratory service providers; psychological service providers (e.g., psychiatrists, psychologists, counselors, social workers); or any other suitable entity. These entities may use the health information to enable the determination of optimal treatments for their patients, to provide or deliver those treatments; and to accurately bill for the associated healthcare services provided to the patients. However, the substantial amount of memory that may be required to use and to store the data generated by the medical devices may result in higher healthcare costs. Further, bulk transmission of data from the medical devices to remote servers may impact network performance by causing higher peak network loads. In addition, waiting for data collection to complete before processing data may prevent health care providers from acting on error information or detecting problems with medical devices as quickly as possible. The use of telemedicine may increase the number of medical devices used by patients in their homes. For example, healthcare professionals may lease the medical devices to patients to use for rehabilitating from an injury or a surgery. A reduction in memory needed for medical devices to properly function may reduce the cost of the medical device and the fees for leasing the medical devices, resulting in reduced healthcare expenses. Further, as bulk transmission of large data files from medical devices may result in higher peak network loads, it may be desirable to reduce the size of individual files being transmitted. Further, transmitting data closer to the time it is generated may enable easier access to error information and faster responses to medical devices on which problems have been detected.

SUMMARY

In general, the present disclosure provides systems and methods for transmitting data and ordering asynchronous data.

In one aspect, a computer-implemented system includes an electromechanical device configured to be manipulated by a patient while performing an exercise session, and a processor in communication with the electromechanical device. The processor is configured to receive data, generate a map packet, and transmit the map packet. The processor is configured to use the data to generate continuity packets, where each of the continuity packets includes a contiguous portion of the data, and transmit the continuity packets. The processor is configured to use the map packet and the continuity packets to cause an output file to be generated.

In one aspect, a system for transmitting data is disclosed. The system includes an information-generating device and a processor in communication with the information-generating device. The processor is configured to receive data; to generate a map packet; to transmit the map packet; using the data, to generate continuity packets, wherein each of the continuity packets comprises a contiguous portion of the data; to transmit the continuity packets; and using the map packet and the continuity packets, to cause an output file to be generated.

In another aspect, a method for operating an information-generating device is disclosed. The method includes receiving data; generating a map packet; transmitting the map packet; using the data to generate continuity packets, wherein each of the continuity packets comprises a contiguous portion of the data; transmitting the continuity packets; and using the map packet and the continuity packets to cause an output file to be generated.

In yet another aspect, a tangible, non-transitory computer-readable storage medium is disclosed. The tangible, non-transitory computer-readable storage medium stores instructions that, when executed, cause a processor to receive data from an information-generating device; to generate a map packet; to transmit the map packet; using the data, to generate continuity packets, wherein each of the continuity packets comprises a contiguous portion of the data; to transmit the continuity packets; and using the map packet and the continuity packets, to cause an output file to be generated.

In yet another aspect, a system for ordering of asynchronously transmitted data is disclosed. The system includes a processor configured to receive, from an information-generating device, a map packet and continuity packets in an initial order. Responsive to receiving the map packet and at least two of the continuity packets, the processor is configured to use the map packet to generate an output file by ordering the continuity packets from the initial order into an output order.

In yet another aspect, a method for operating a computing device is disclosed. The method includes receiving, from an information-generating device, a map packet and continuity packets in an initial order, and, responsive to receiving the map packet and at least two of the continuity packets, using the map packet to generate an output file by ordering the continuity packets from the initial order into an output order.

In yet another aspect, a tangible, non-transitory computer-readable storage medium is disclosed. The tangible, non-transitory computer-readable storage medium stores instructions that, when executed, cause a processor to receive, from an information-generating device, a map packet and continuity packets in an initial order. Responsive to receiving the map packet and at least two of the continuity packets, the instructions cause the processor to use the map packet to generate an output file by ordering the continuity packets from the initial order into an output order.

In yet another aspect, a system for transmission and ordering of asynchronous data is disclosed. The system comprises an information-generating device comprising a device-side processor. The device-side processor is configured to receive data; generate a map packet; transmit the map packet; use the data to generate continuity packets, wherein each of the continuity packets comprises a contiguous portion of the data; and transmit the continuity packets. The system further comprises a remote computing device comprising a remote processor. The remote processor is configured to receive, from the information-generating device, the map packet; to receive, from the information-generating device, the continuity packets in an initial order; and responsive to receiving at least two of the continuity packets and the map packet, to use the map packet to generate an output file by ordering the continuity packets from the initial order into an output order.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, independent of whether those elements are in physical contact with one another. The terms "transmit," "receive," and "communicate," as well as derivatives thereof, encompass both direct and indirect communication. The terms "transmit," "receive," and "communicate," as well as derivatives thereof, encompass both communication with remote systems and communication within a system, including reading and writing to different portions of a memory device. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable storage medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable storage medium" includes any type of medium capable of being accessed by a computer, such as read only memory (ROM), random access memory (RAM), a hard disk drive, a flash drive, a compact disc (CD), a digital video disc (DVD), solid state drive (SSD), or any other type of memory. A "non-transitory" computer readable storage medium excludes wired, wireless, optical, or other communication links that transport transitory electrical or other signals. A non-transitory computer-readable storage medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

FIGS. 1-5, discussed below, and the various embodiments used to describe the principles of this disclosure are by way of illustration only and should not be construed in any way to limit the scope of the disclosure.

Figure 1:
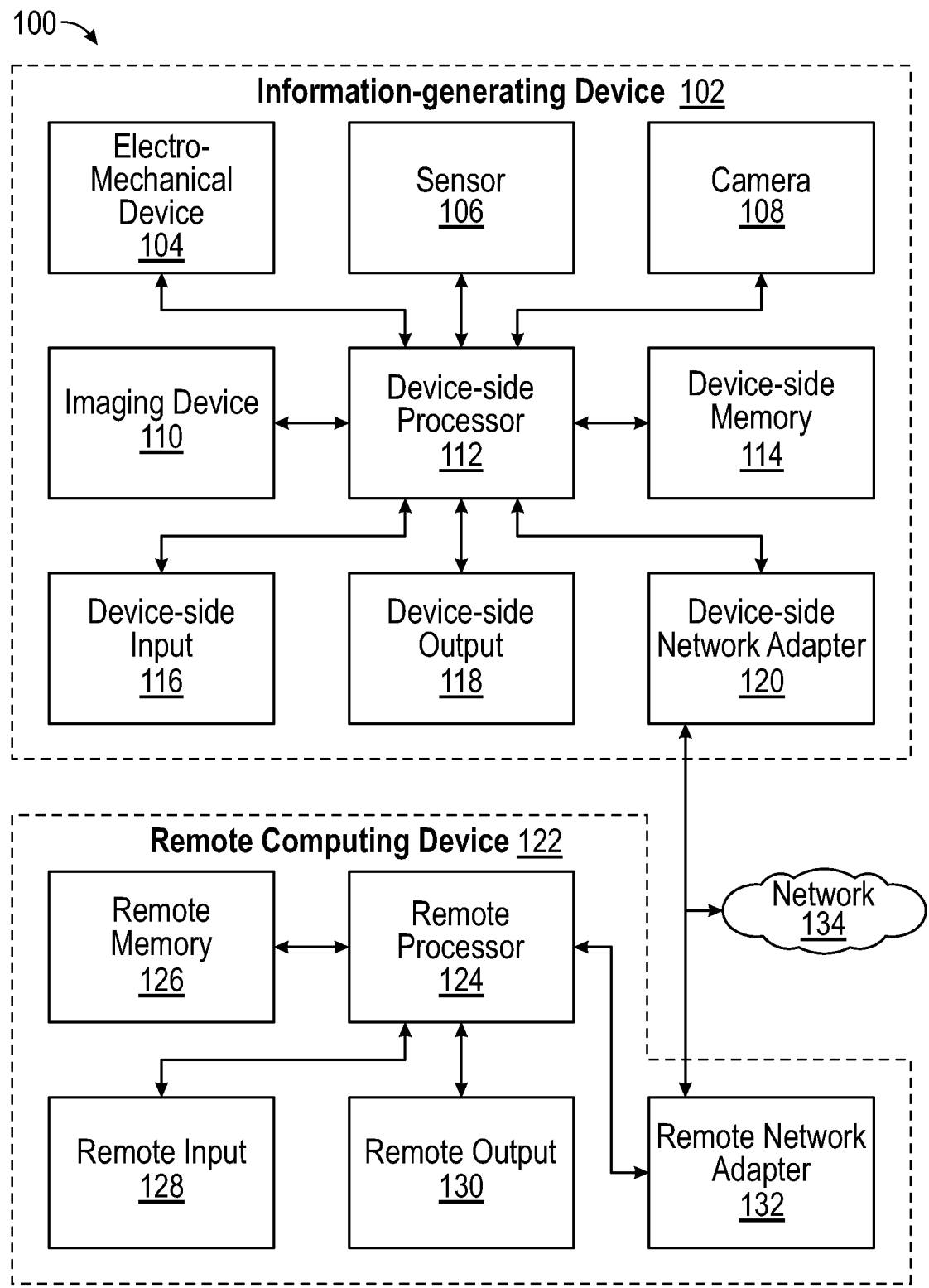
FIG. 1 illustrates a component diagram of an illustrative system for transmitting and ordering asynchronous data according to certain aspects of this disclosure.
Figure 2:
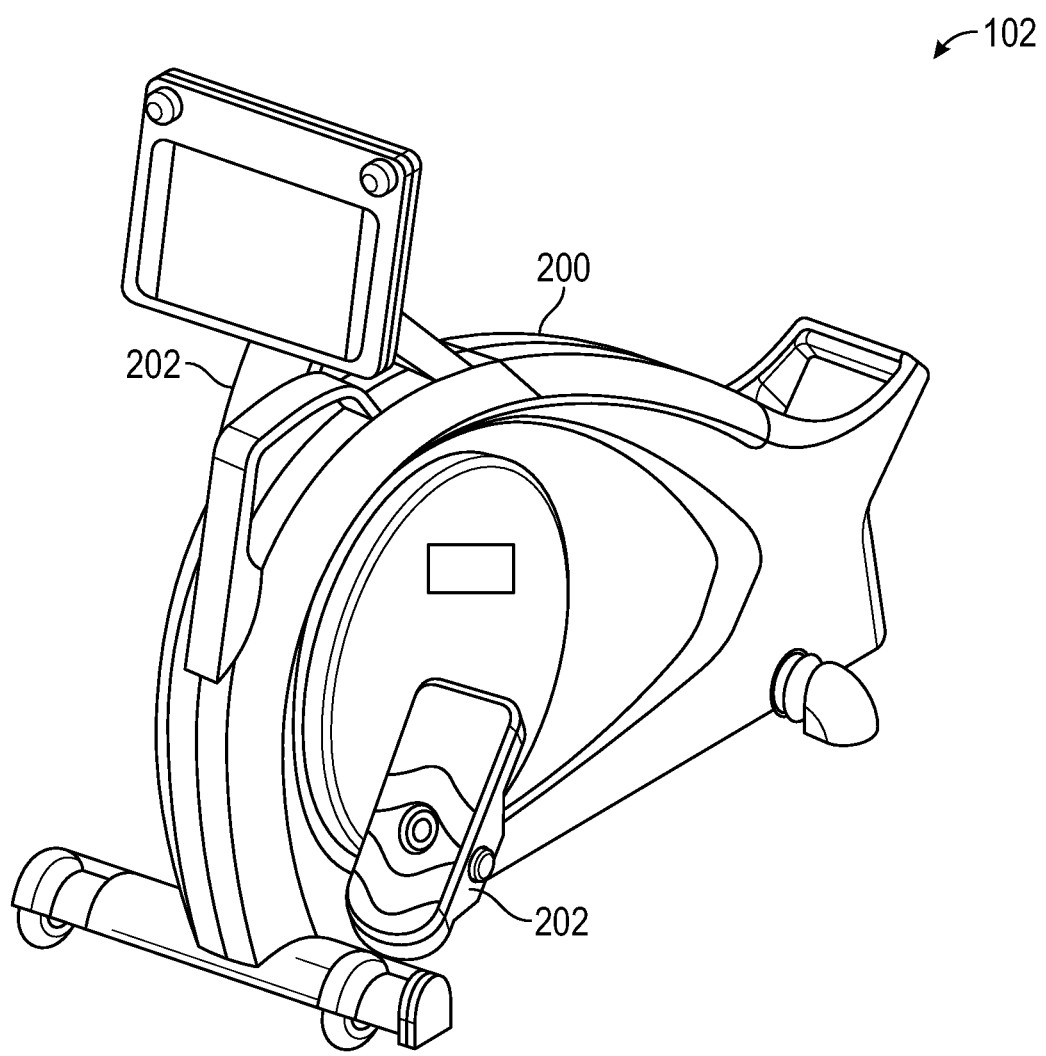
FIG. 2 illustrates an example information-generating device according to certain aspects of this disclosure.

FIG. 1 illustrates a component diagram of an illustrative system 100 for transmitting and ordering asynchronous data in accordance with aspects of this disclosure. The system 100 may include an information-generating device 102. The information-generating device 102 may be a medical device. The medical device may be a testing device, a diagnostic device, a therapeutic device, or any other suitable medical device. "Medical device" as used in this context may refer to hardware, software, or a mechanical or other device that may assist in a medical service, regardless of whether it is FDA (or other governmental regulatory body of any given country) approved, required to be FDA (or other governmental regulatory body of any given country) approved or available commercially or to consumers without such approval. Non-limiting examples of the medical devices include an insulin pump, a thermometer, an MRI machine, a CT-scan machine, a glucose meter, an apheresis machine, and a physical therapy machine (e.g., an orthopedic rehabilitation device, such as a physical therapy cycle). Non-limiting examples of places where the medical device may be located include a healthcare clinic, a physical rehabilitation center, and a user's home to allow for telemedicine treatment, rehabilitation, and/or testing. FIG. 2 illustrates an example of the information-generating device 102 in which the information-generating device 102 is a physical therapy cycle 200.

The information-generating device 102 may include an electromechanical device 104, such as pedals 202 of the physical therapy cycle 200, a goniometer configured to attach to a joint and measure joint angles, or any other suitable electromechanical device. The electromechanical device 104 may be configured to be manipulated by a patient while performing an exercise session. The electromechanical device 104 may be configured to transmit information, such as pedal position information. A non-limiting example of positioning information includes information relating to the location of the electromechanical device 104 (e.g., the pedals 202).

The information-generating device 102 may include a sensor 106. The sensor 106 can be used for obtaining information, such as fingerprint information, retina information, voice information, height information, weight information, vital sign information (e.g., blood pressure, heart rate, etc.), response information to physical stimuli (e.g., change in heart rate while running on a treadmill), performance information (rate of speed of rotation of the pedals 202 of the physical therapy cycle 200), or any other suitable information. The sensor 106 may be a temperature sensor (such as a thermometer or thermocouple), a strain gauge, a proximity sensor, an accelerometer, an inclinometer, an infrared sensor, a pressure sensor, a light sensor, a smoke sensor, a chemical sensor, any other suitable sensor, a fingerprint scanner, a sound sensor, a microphone, or any combination thereof. The sensor 106 may be located on an interior or exterior of the device. For example, the sensor 106 may be a pedal position sensor located on the pedals 202 of the physical therapy cycle 200.

The information-generating device 102 may include a camera 108, such as a still image camera, a video camera, an infrared camera, an X-ray camera, any other suitable camera, or any combination thereof. The information-generating device 102 may include an imaging device 110, such as an MRI imaging device, an X-ray imaging device, a thermal imaging device, any other suitable imaging device, or any combination thereof. The information-generating device 102 may include a device-side processor 112. The device-side processor 112 can include, for example, computers, intellectual property (IP) cores, application-specific integrated circuits (ASICs), programmable logic arrays, optical processors, programmable logic controllers, microcode, microcontrollers, servers, microprocessors, digital signal processors, any other suitable circuit, or any combination thereof. The device-side processor may be in communication with the electromechanical device 104, the sensor 106, the camera 108, the imaging device 110, any other suitable device, or any combination thereof.

The information-generating device 102 may include a device-side memory 114 in communication with the device-side processor 112. The device-side memory 114 can include any type of memory capable of being accessed by a computer, such as read only memory (ROM), random access memory (RAM), a hard disk drive, a flash drive, a compact disc (CD), a digital video disc (DVD), solid state drive (SSD), or any other suitable type of memory. The device-side memory 114 may store instructions that cause the device-side processor 112 to perform a series of actions or processes.

The information-generating device 102 may include a device-side input 116 in communication with the device-side processor 112. Examples of the device-side input 116 include a keyboard, a keypad, a mouse, a microphone supported by speech-to-text software, or any other suitable input device. The device-side input 116 may be used by a medical system operator to input information, such as user-identifying information, observational notes, or any other suitable information. An operator is to be understood throughout this disclosure to include people, bots, robots, hardware, and/or computer software, such as programs or artificial intelligence, and any combination thereof.

The information-generating device 102 may include a device-side output 118 in communication with the device-side processor 112. The device-side output 118 may be used to provide information to the operator or a user (or patient) of the information-generating device 102. For the purposes of this disclosure, user and patient are used interchangeably. Examples of the device-side output 118 may include a display screen, a speaker, an alarm system, or any other suitable output device, including haptic, tactile, olfactory, or gustatory ones. In some embodiments, such as where the information-generating device 102 includes a touchscreen, the device-side input 116 and the device-side output 118 may be the same device.

For communicating with remote computers and servers, the information-generating device 102 may include a device-side network adapter 120 in communication with the device-side processor 112. The device-side network adapter 120 may include wired or wireless network adapter devices (e.g., a wireless modem or Bluetooth) or a wired network port.

The information-generating device 102 may be coupled to or be in communication with a remote computing device 122. The remote computing device 122 may include a remote processor 124. The remote processor 124 can include, for example, computers, intellectual property (IP) cores, application-specific integrated circuits (ASICs), programmable logic arrays, optical processors, programmable logic controllers, microcode, microcontrollers, servers, microprocessors, digital signal processors, any other suitable circuit, or any combination thereof.

The remote computing device 122 may include a remote memory 126 in communication with the remote processor 124. The remote memory 126 can include any type of memory capable of being accessed by a computer, such as read only memory (ROM), random access memory (RAM), a hard disk drive, a flash drive, a compact disc (CD), a digital video disc (DVD), solid state drive (SSD), or any other suitable type of memory. The remote memory 126 may store instructions that cause the remote processor 124 to perform a series of actions or processes.

The remote computing device 122 may include a remote input 128 in communication with the remote processor 124. Examples of the remote input 128 include a keyboard, a keypad, a mouse, a microphone supported by speech-to-text software, or any other suitable input device. The remote input 128 may be used by a medical system operator to input information, such as user-identifying information, observational notes, or any other suitable information. An operator is to be understood throughout this disclosure to include people, bots, robots, hardware, and/or computer software, such as programs or artificial intelligence, and any combination thereof.

The remote computing device 122 may include a remote output 130 in communication with the remote processor 124. The remote output 130 may be used to provide information to the operator or a user (or patient) of the remote computing device 122. For the purposes of this disclosure, user and patient are used interchangeably. Examples of the remote output 130 may include a display screen, a speaker, an alarm system, or any other suitable output device, including haptic, tactile, olfactory, or gustatory ones. In some embodiments, such as where the remote computing device 122 includes a touchscreen, the remote input 128 and the remote output 130 may be the same device.

For communicating with the information-generating device 102, as well as remote computers and servers, the remote computing device 122 may include a remote network adapter 132 in communication with the remote processor 124. The remote network adapter 122 may include wired or wireless network adapter devices (e.g., a wireless modem or Bluetooth) or a wired network port.

Both the device-side network adapter 120 and the remote network adapter 132 may be in communication with a network 134. Transmissions between the information-generating device 102 and the remote computing device 122 may pass through the network 134. The network 134 may be a public network (e.g., connected to the Internet via wired (Ethernet) or wireless (Wi-Fi)), a private network (e.g., a local area network (LAN) or wide area network (WAN)), a combination thereof, or any other suitable network.

Any time information is transmitted or communicated, the information may be in EDI file format or any other suitable file format. In any of the processes or steps of the method, file format conversions may take place. By utilizing Internet of Things (IoT) devices or gateways, data streams, ETL bucketing, EDI mastering, or any other suitable technique, data can be mapped, converted, translated, or transformed into a carrier-preferred state. As a result of the volume of data being transmitted, the data security requirements, and the data consistency requirements, an enterprise grade architecture may be utilized for reliable data transfer.

FIG. 1 is not intended to be limiting: the system 100, the information-generating device 102, and the remote computing device 122 may include more or fewer components than those illustrated in FIG. 1.

Figure 3A:
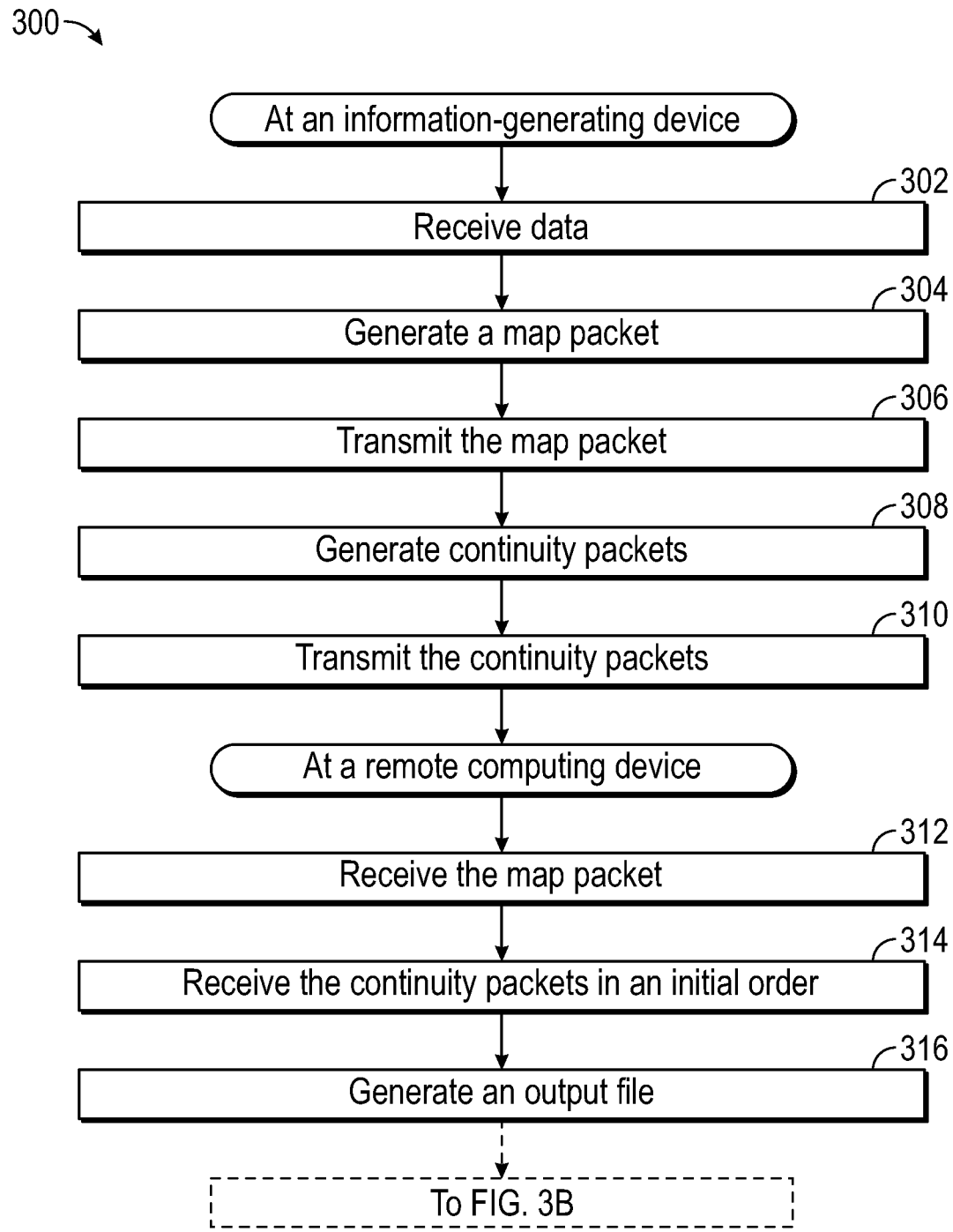
FIGS. 3A and 3B illustrate a method for transmitting data and ordering asynchronous data according to certain aspects of this disclosure.
Figure 3B:
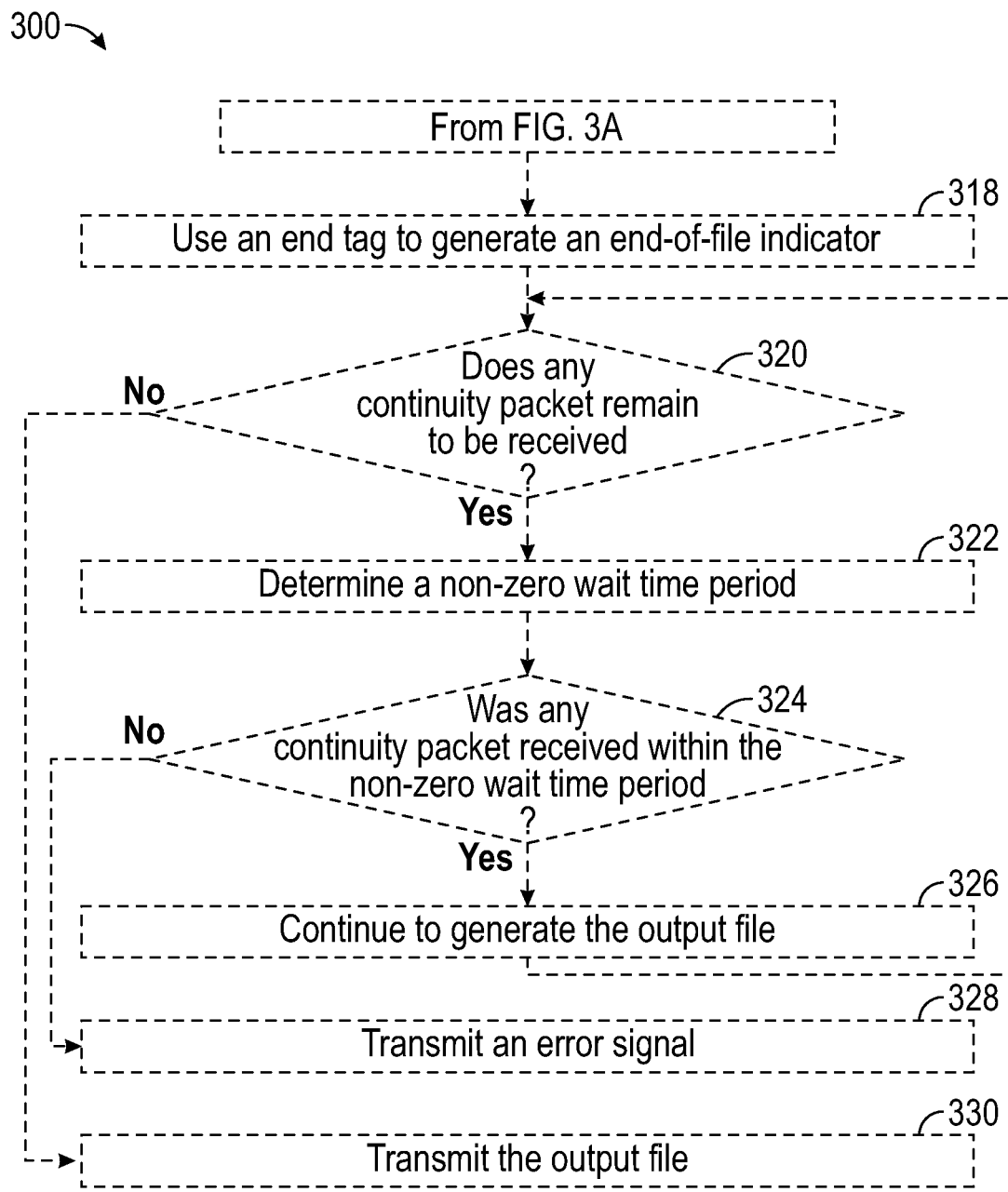

FIGS. 3A and 3B illustrate a computer-implemented method 300 for transmitting data and ordering asynchronous data. The method 300 may be performed by the system 100 using the information-generating device 102 and the remote computing device 122. The method 300 may be implemented on a pair of processors, such as the device-side processor 112 and the remote processor 124, which are together configured to perform the steps of the method 300. The method 300 may include operations implemented in instructions stored on one or more memory devices, such as the device-side memory 114 and the remote memory 126, and be executed by one or more processors, such as the device-side processor 112 and the remote processor 124. The steps of the method 300 may be stored in one or more non-transient computer-readable storage media.

At step 302, the method 300 includes, at the information-generating device 102, receiving data. For example, the device-side processor 112 can receive data from the electromechanical device 104, the sensor 106, the camera, 108, the imaging device 110, the device-side input 116, or any other suitable device. As a more specific example, the device-side processor 112 may receive an MII image from an MII imaging device (i.e., the imaging device 110). The data may be received as a stream of data. The stream of data may be a continuous stream of data. The device-side processor 112 may initially receive the data as a digital signal, an analog signal, or any other suitable signal. The device-side processor 112 may convert data from an analog signal to a digital signal.

At step 304, the method 300 includes, at the information-generating device, generating a map packet. The map packet contains data mapping information that indicates a means, a method, an approach or another mechanism for receiving the continuity packets. In some embodiments, the map packet includes end-of-file information that function as information against which data from later-received continuity packets can be compared for determining whether data transmission for a given file has ended. For example, the map packet may contain data mapping information indicating that the continuity packets will have a header following the format of "AA######AA", and an end-of-file continuity packet will have an end-of-file header following the format of "AA######ZZ". In this example, "######" indicates a numerical value starting at "000000" and going to a possible maximum of "999999" and "ZZ" functions as an end tag to indicate that the tagged continuity packet is the final continuity packet of the given file.

At step 306, the method 300 includes, at the information-generating device, transmitting the map packet. For example, the device-side processor 112 may direct the device-side network adapter 120 to transmit the map packet to the remote network adapter 132 of the remote computing device 122.

At step 308, the method 300 includes, at the information-generating device, generating the continuity packets. Each of the continuity packets is a data packet that includes a contiguous portion of the data. The continuity packets may be generated using the data. For example, the device-side processor 112 may take a contiguous portion of the data and place that contiguous portion into one of the continuity packets. One or more of the continuity packets may include header information that the processor can use to order the continuity packets. For example, a first continuity packet may include a first header including first header information of "AA000000AA", and a second continuity packet may include a second header including second header information of "AA000001AA". A contiguous portion of the data mapping information of the map packet may correspond to a contiguous portion of the header information. For example, the header information may include a contiguous portion of data, including the string "AA". The string "AA" corresponds with a portion of the mapping information of the map packet, thereby indicating that header information of relevant continuity packets will contain the string "AA". The header information may also include information pertaining to the portion of data contained in the continuity packet. The information-generating device generates the continuity packets in an initial order; however, a remote computing device 122 may not receive the continuity packets in the initial order (e.g., a first continuity packet may be generated first and a second continuity packet may be generated second, but the second packet may be received before the first packet is received). Thus, the header information may include information that the remote computing device 122 can use to order (e.g., reassemble) the continuity packets, such as the initial order that the continuity packets were generated. The header information of an end-of-file continuity packet can include an end tag corresponding to a contiguous portion of the end-of-file information. For example, an end-of-file continuity packet may include end-of-file header information of "AA000002ZZ", where "ZZ" functions as the end tag. The generation of the continuity packets may occur all at once or be spread out over time as more data is received, so the end-of file header information is used to indicate an end of the data stream.

At step 310, the method 300 includes, at the information-generating device, transmitting the continuity packets. For example, the device-side processor 112 may direct the device-side network adapter 120 to transmit the continuity packets to the remote network adapter 132 of the remote computing device 122. This transmission may occur after all continuity packets have been generated, as the continuity packets are being generated, or any combination thereof. In cases where the generation of the continuity packets is spread out over time as more data is received, the generation and the transmission of the continuity packets allow for a reduced memory requirement and reduced peak network loads relative to first waiting for all of the data to be received. For instance, if, before generating the continuity packets, the information-generating device waits until all of the data is received (e.g., from the sensors), the device-side memory 114 may have to store the entirety of the data (i.e., which may require a substantial amount of memory to store an extremely large file), rather than temporarily storing a portion of the data while the device-side processor 112 generates and transmits each continuity packet. Similarly, if, before transmitting the continuity packets, the information-generating device waits until all of the data has been received and all of the continuity packets have been generated, the network loads required for the transmission may be higher because a larger amount of data is being transmitted at once (e.g., all of the continuity packets are being transmitted in a short time period).

At step 312, the method 300 includes, at the remote computing device (e.g., the remote computing device 122), receiving the map packet. The map packet may be received from the information-generating device 102. For example, the remote computing device 122 may receive the map packet by way of the remote network adapter 132.

At step 314, the method 300 includes, at the remote computing device, receiving continuity packets in an initial order. The continuity packets may be received from the information-generating device 102. For example, continuity packets may be received by the remote computing device 122 by way of the remote network adapter 132 in an initial order wherein the second continuity packet is received first, the first continuity packet is received second, and the end-of-file continuity packet is received third.

At step 316, the method 300 includes, at the remote computing device, generating an output file. Responsive to receiving at least two of the continuity packets and the map packet, the map packet may be used to generate an output file. The output file may be generated by ordering the continuity packets from the initial order into an output order. For example, given the initial order described above in step 314, the remote processor 124 may order the continuity packets, or contiguous portions of the continuity packets corresponding to contiguous portions of the data, into an output order. The output order may be as follows: 1) the first continuity packet, 2) the second continuity packet, and 3) the end-of-file continuity packet. In some embodiments, as the remote processor receives the continuity packets, the remote processor may contemporaneously generate the output file. For example, the remote computing device 124 may receive the second continuity packet first and the first continuity packet second, but not yet have received the end-of-file continuity packet, in which case the remote processor 124 may order the continuity packets into an output order having the first continuity packet first and the second continuity packet second. In some embodiments, while the output file is being generated, the continuity packets are configured to be readable by external processes. Examples of such external processes include maintenance processes configured to check for device maintenance status or error messages. Such external processes may be able to read and/or respond to maintenance requests or errors prior to ordering, such that an error message contained in the continuity packets can be read prior to completing the generation of the output file. For example, if a patient is undergoing a CT scan performed by a CT scanner, a processor may monitor and read the data in real-time or near real-time to detect an error message. In this example, if the CT scanner generates a continuity packet containing an error message indicating a fault with the CT scanner (e.g., the data obtained by the CT scanner will be unusable), then, at the direction of such an external monitoring process, the remote processor 124 may read the error message prior to ordering and generating the output file and stop the CT scanner during the CT scan. Stopping the CT scan prior to its completion would limit the patient's unnecessary exposure to X-rays, as any exposure after the error may not result in usable data.

At step 318, the method 300 may include, at the remote computing device, using the end tag to generate an end-of-file indicator. For example, a flag may be used or a variable may be set as an end-of-file indicator when the end-of-file continuity packet containing the end tag "ZZ" is received (i.e., the remote processor may change a variable "end-of-file-reached" from "false" to "true").

At step 320, the method 300 may include using the header information, the map packet, and the end-of-file indicator to determine whether any continuity packets remain to be received. For example, if the first continuity packet containing the first header information of "AA000000AA" and the end-of-file continuity packet containing the end-of-file header information "AA000002ZZ" (and thus the end tag "ZZ") have been received, the remote processor 124 may determine that the second continuity packet has not been received. If any continuity packets remain to be received, the method 300 proceeds to step 322. If all continuity packets have been received, the method 300 proceeds to step 330.

At step 322, if any continuity packets remain to be received, the method 300 may include determining a non-zero wait time period. For example, if the second continuity packet has not been received, the remote processor 124 may determine a wait time period. The wait time period may be between two seconds and ten seconds, or any other suitable period of time.

At step 324, the method 300 may include, at the remote computing device, determining if any continuity packets were received within the wait time period. For example, if the second continuity packet, which had not been previously received, is received within the wait time period, the remote computing device may determine that a continuity packet was received within the wait time period, subsequent to which the method 300 proceeds to step 326. However, if the second continuity packet is not received within the wait time period, the remote processor 124 may determine that the continuity packet was not received within the wait time period, subsequent to which the method 300 proceeds to step 328.

At step 326, responsive to receiving another continuity packet within the non-zero wait time period, the method 300 may include the remote computing device continuing to generate the output file. For example, if the determination is that the second continuity packet that had not been previously received is received within the wait time period, then the remote processor 124 may continue generating the output file. The method 300 may return to step 320.

At step 328, responsive to determining the non-zero wait time period and not receiving another continuity packet within the non-zero wait time period, the method 300 may include the remote computing device transmitting an error signal. For example, if the determination is that the second continuity packet that had not been previously received was not received within the wait time period, the remote processor 124 may direct the remote network adapter 132 to transmit an error message and/or the remote output 130 to present the error message (e.g., "Error: Incomplete Data").

At step 330, responsive to determining that every continuity packet has been received, the method 300 includes transmitting the output file. For example, if the first continuity packet, the second continuity packet, and the end-of-file continuity packet have been received and ordered (e.g., into an output file), the remote processor 124 may direct the remote network adapter 132 to transmit the output file via the network 134.

Figure 4:
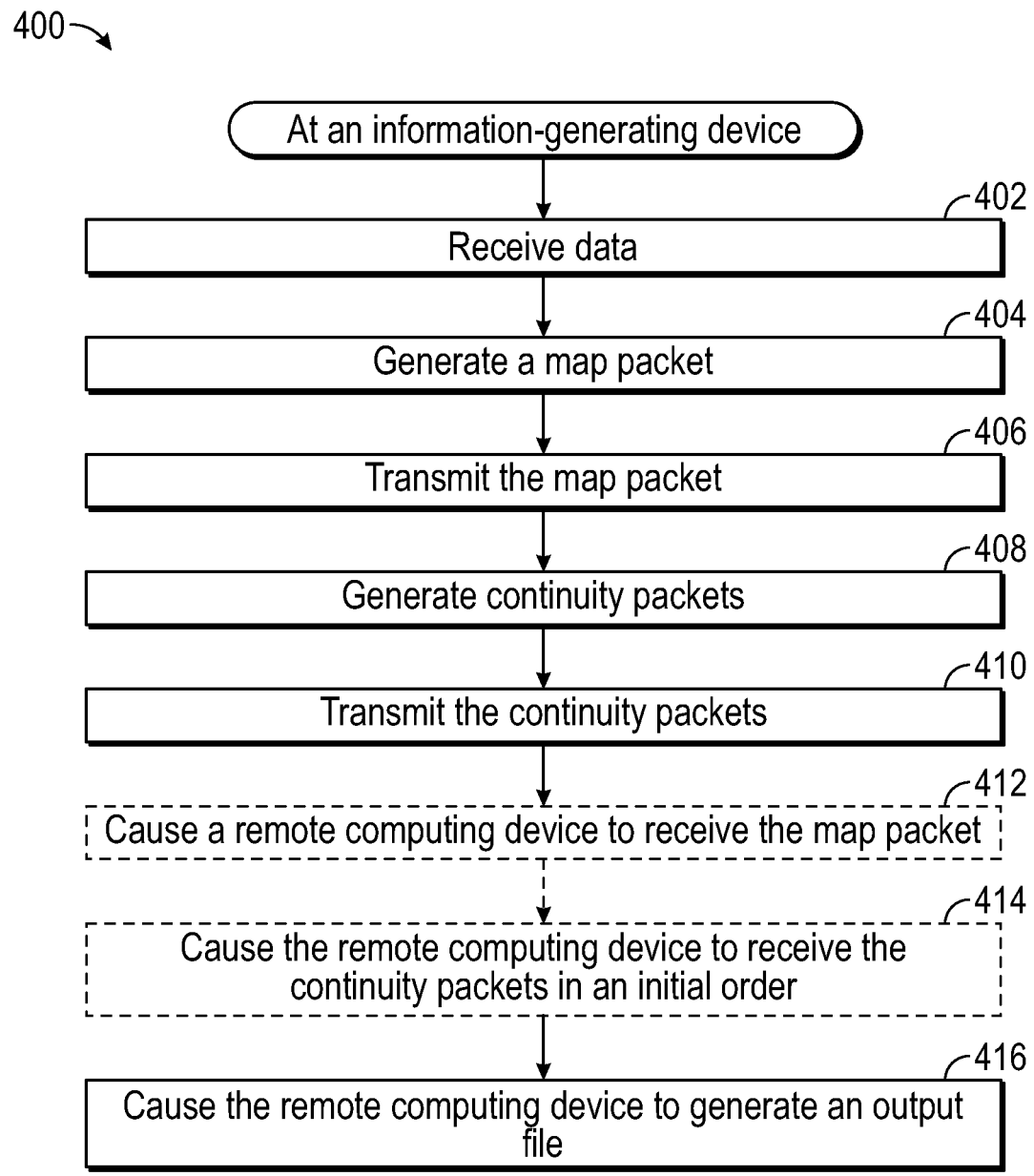
FIG. 4 illustrate a method for transmitting data according to certain aspects of this disclosure.

FIG. 4 illustrates a computer-implemented method 400 for transmitting data. Using the information-generating device 102, the method 400 may be performed by the system 100. The method 400 may be implemented on a processor, such as the device-side processor 112 configured to perform the steps of the method 400. The method 400 may include operations implemented in instructions stored on a memory device, such as the device-side memory 114 executed by a processor, such as the device-side processor 112. The steps of the method 300 may be stored on a non-transient computer-readable storage medium.

At step 402, the method 400 includes, at the information-generating device (e.g., the information-generating device 102), receiving data. For example, the device-side processor 112 can receive data from the electromechanical device 104, the sensor 106, the camera 108, the imaging device 110, the device-side input 116, or any other suitable device. As a more specific example, the device-side processor 112 may receive an MM image from an MM imaging device (i.e., the imaging device 110). The data may be received as a stream of data. The stream of data may be a continuous stream of data. The device-side processor 112 may initially receive the data as a digital signal, an analog signal, or any other suitable signal. The device-side processor 112 may convert data from an analog signal to a digital signal.

At step 404, the method 400 includes, at the information-generating device, generating a map packet. The map packet contains data mapping information that indicates a means, a method, an approach, or another mechanism for receiving the continuity packets. In some embodiments, the map packet includes end-of-file information that function as information against which data from later-received continuity packets can be compared for determining whether data transmission for a given file has ended. For example, the map packet may contain data mapping information indicating that the continuity packets will have a header following the format of "AA######AA", and an end-of-file continuity packet will have an end-of-file header following the format of "AA######ZZ". In this example, "######" indicates a numerical value starting at "000000" and going to a possible maximum of "999999" and "ZZ" functions as an end tag to indicate that the tagged continuity packet is the final continuity packet of the given file.

At step 406, the method 400 includes, at the information-generating device, transmitting the map packet. For example, the device-side processor 112 may direct the device-side network adapter 120 to transmit the map packet to the remote network adapter 132 of the remote computing device 122.

At step 408, the method 400 includes, at the information-generating device, generating the continuity packets. Each of the continuity packets is a data packet that includes a contiguous portion of the data. The continuity packets may be generated using the data. For example, the device-side processor 112 may take a contiguous portion of the data and place that contiguous portion into one of the continuity packets. One or more of the continuity packets may include header information that the processor can use to order the continuity packets. For example, a first continuity packet may include a first header including first header information of "AA000000AA", and a second continuity packet may include a second header including second header information of "AA000001AA". A contiguous portion of the data mapping information of the map packet may correspond to a contiguous portion of the header information. For example, the header information may include a contiguous portion of data including the string "AA". The string "AA" corresponds to a portion of the mapping information of the map packet, indicating that header information of relevant continuity packets will contain the string "AA". The header information may also include information pertaining to the portion of data contained in the continuity packet. The information-generating device generates the continuity packets in an initial order; however, a remote computing device 122 may not receive the continuity packets in the initial order (e.g., a first continuity packet may be generated first and a second continuity packet may be generated second, but the second packet may be received before the first packet has been received). Thus, the header information may include information that the remote computing device 122 can use to order (e.g., reassemble) the continuity packets, such as the initial order that the continuity packets were generated. The header information of an end-of-file continuity packet can include an end tag corresponding to a contiguous portion of the end-of-file information. For example, an end-of-file continuity packet may include end-of-file header information of "AA000002ZZ", where "ZZ" functions as the end tag. The generation of the continuity packets may occur all at once or be spread out over time as more data is received, so the end-of file header information may be used to indicate an end of the data stream.

At step 410, the method 400 includes, at the information-generating device, transmitting the continuity packets. For example, the device-side processor 112 may direct the device-side network adapter 120 to transmit the continuity packets to the remote network adapter 132 of the remote computing device 122. This transmission may occur after all continuity packets have been generated, as the continuity packets are being generated, or any combination thereof. In cases where the generation of the continuity packets is spread out over time as more data is received, the generation and the transmission of the continuity packets allow for a reduced memory requirement and reduced peak network loads relative to waiting for all of the data to be received. For instance, if, before generating the continuity packets, the information-generating device waits until all of the data is received (e.g., from the sensors), the device-side memory 114 may have to store the entirety of the data (i.e., which may require a substantial amount of memory to store an exceedingly large file), rather than temporarily storing a portion of the data while the device-side processor 112 generates and transmits each continuity packet. Similarly, if, before transmitting the continuity packets, the information-generating device waits until all of the data has been received and all of the continuity packets have been generated, the network loads required for the transmission may be higher because a larger amount of data is being transmitted at once (e.g., all of the continuity packets are being transmitted in a short time period). The method 400 may proceed to step 412 or step 416.

At step 412, the method 400 may include causing the remote computing device (e.g., the remote computing device 122) to receive the map packet. The map packet may be received from the information-generating device 102. For example, the remote computing device 122 may receive the map packet by way of the remote network adapter 132.

At step 414, the method 400 may include causing the remote computing device to receive continuity packets in an initial order. The continuity packets may be received from the information-generating device 102. For example, continuity packets may be received by the remote computing device 122 by way of the remote network adapter 132 in an initial order where the second continuity packet is received first, the first continuity packet is received second, and the end-of-file continuity packet is received third.

At step 416, the method 400 includes, at the remote computing device, generating an output file. Responsive to receiving at least two of the continuity packets and the map packet, the map packet may be used to generate an output file. The output file may be generated by ordering the continuity packets from the initial order into an output order. For example, given the initial order described above in step 414, the remote processor 124 may order the continuity packets, or contiguous portions of the continuity packets corresponding to contiguous portions of the data, into an output order. The output order may be as follows: 1) the first continuity packet, 2) the second continuity packet, and 3) the end-of-file continuity packet. In some embodiments, as the remote processor receives the continuity packets, the remote processor may contemporaneously generate the output file. For example, the remote computing device 124 may receive the second continuity packet first and the first continuity packet second, but not yet have received the end-of-file continuity packet, after which the remote processor 124 may order the continuity packets into an output order having the first continuity packet first and the second continuity packet second. In some embodiments, while the output file is being generated, the continuity packets are configured to be readable by external processes. Examples of such external processes include maintenance processes configured to check for device maintenance status or error messages. Such external process may be able to read and/or respond to maintenance requests or errors prior to ordering, such that an error message contained in the continuity packets can be read prior to completing the generation of the output file. For example, if a patient is undergoing a CT scan performed by a CT scanner, a processor may monitor and read the data in real-time or near real-time to detect an error message. In this example, if the CT scanner generates a continuity packet containing an error message indicating a fault with the CT scanner (e.g., the data obtained by the CT scanner will be unusable), then, at the direction of such an external monitoring process, the remote processor 124 may read the error message prior to ordering and generating the output file and stop the CT scanner during the CT scan. Stopping the CT scan prior to its completion would limit the patient's unnecessary exposure to X-rays, as any exposure after the error may not result in usable data.

Figure 5A:
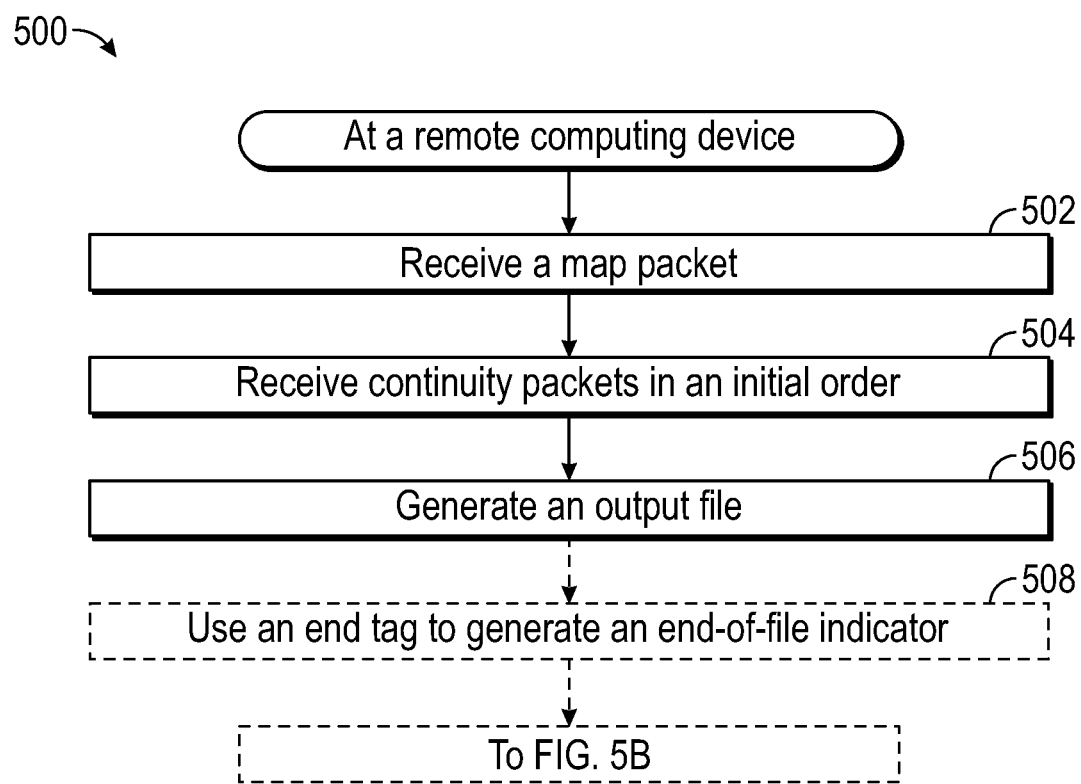
FIGS. 5A and 5B illustrate a method for ordering asynchronous data according to certain aspects of this disclosure.
Figure 5B:
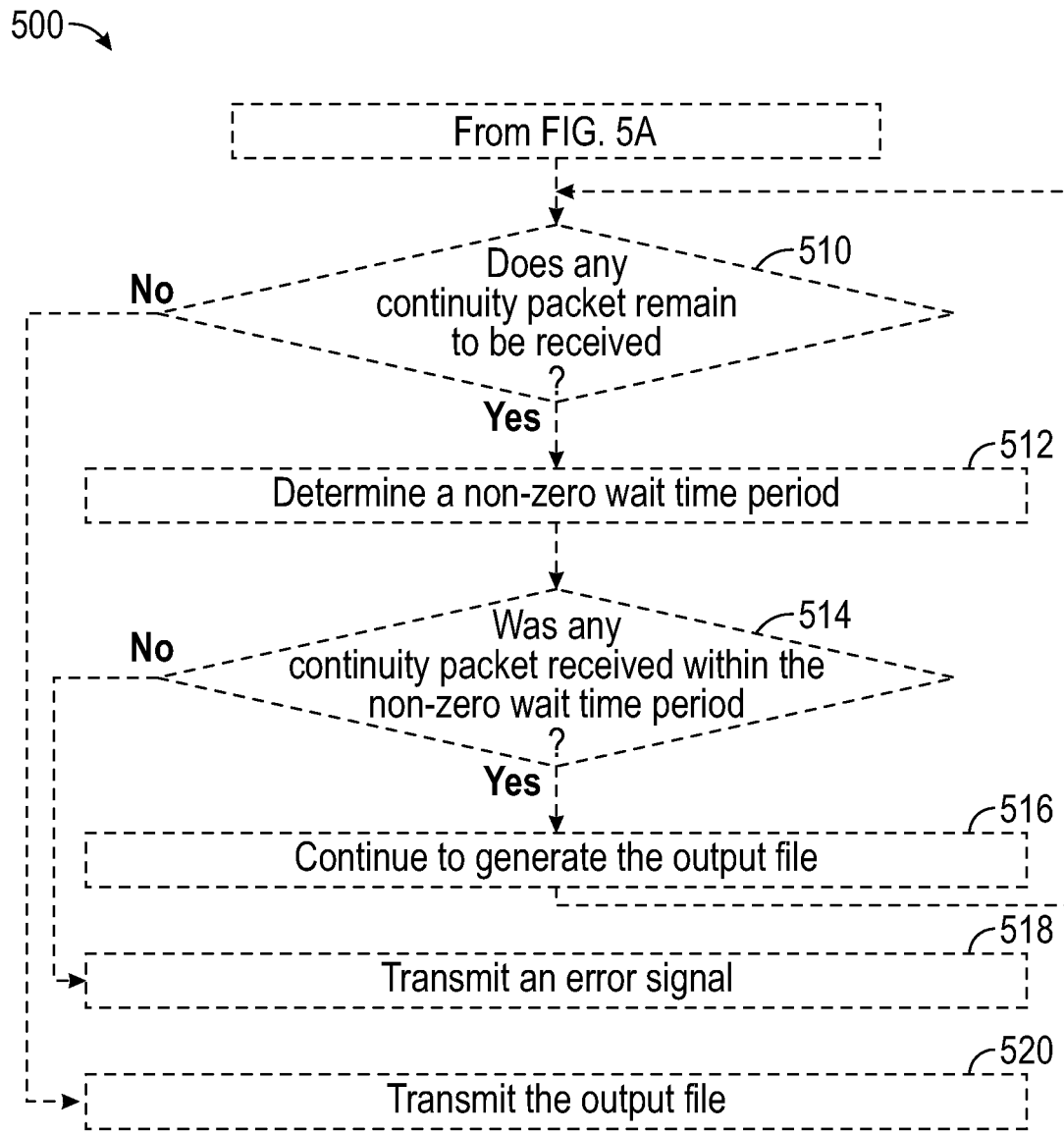

FIGS. 5A and 5B illustrate a computer-implemented method 500 for ordering asynchronous data. The method 500 may be performed by the system 100 using the remote computing device 122. The method 500 may be implemented on a processor, such as the remote processor 124, configured to perform the steps of the method 500. The method 500 may include operations implemented in instructions stored on a memory devices, such as the remote memory 126, and executed on a processor, such as the remote processor 124. The steps of the method 500 may be stored in one or more non-transient computer-readable storage media.

At step 502, the method 500 includes, at the remote computing device (e.g., the remote computing device 122), receiving the map packet. The map packet may be received from the information-generating device 102. For example, the remote computing device 122 may receive the map packet by way of the remote network adapter 132. The map packet contains data mapping information that functions as an indicator of how continuity packets will be received. In some embodiments, the map packet includes end-of-file information that function as information against which data from later-received continuity packets can be compared for determining whether data transmission for a given file has ended. For example, the map packet may contain data mapping information indicating that the continuity packets will have a header following the format of "AA######AA", and an end-of-file continuity packet will have an end-of-file header following the format of "AA######ZZ". In this case, "######" indicates a numerical value starting at "000000" and going to a possible maximum of "999999" and "ZZ" functions as an end tag to indicate that the tagged continuity packet is the final continuity packet of the given file.

At step 504, the method 500 includes, at the remote computing device, receiving continuity packets in an initial order. The continuity packets may be received from the information-generating device 102. For example, continuity packets may be received by the remote computing device 122 by way of the remote network adapter 132 in an initial order where the second continuity packet is received first, the first continuity packet is received second, and the end-of-file continuity packet is received third. Each of the continuity packets is a data packet that includes a contiguous portion of the data. The continuity packets may be generated using the data. For example, the device-side processor 112 may take a contiguous portion of the data and place that contiguous portion into one of the continuity packets. One or more of the continuity packets may include header information that the processor can use to order the continuity packets. For example, a first continuity packet may include a first header including first header information of "AA000000AA", and a second continuity packet may include a second header including second header information of "AA000001AA". A contiguous portion of the data mapping information of the map packet may correspond to a contiguous portion of the header information. For example, the header information may include a contiguous portion of data including the string "AA". The string "AA" corresponds to a portion of the mapping information of the map packet, indicating that header information of relevant continuity packets will contain the string "AA." The header information may also include information pertaining to the portion of data contained in the continuity packet. The information-generating device generates the continuity packets in an initial order; however, a remote computing device 122 may not receive the continuity packets in the initial order (e.g., a first continuity packet may be generated first and a second continuity packet may be generated second, but the second packet may be received before the first packet is received). Thus, the header information may include information that the remote computing device 122 can use to order (e.g., reassemble) the continuity packets, such as in the initial order that the continuity packets were generated. The header information of an end-of-file continuity packet can include an end tag corresponding to a contiguous portion of the end-of-file information. For example, an end-of-file continuity packet may include end-of-file header information of "AA000002ZZ", where "ZZ" functions as the end tag.

At step 506, the method 500 includes, at the remote computing device, generating an output file. Responsive to receiving at least two of the continuity packets and the map packet, the map packet may be used to generate an output file. The output file may be generated by ordering the continuity packets from the initial order into an output order. For example, given the initial order described above in step 504, the remote processor 124 may order the continuity packets, or contiguous portions of the continuity packets corresponding to contiguous portions of the data, into an output order. The output order may be as follows: 1) the first continuity packet, 2) the second continuity packet, and 3) the end-of-file continuity packet. In some embodiments, as the remote processor receives the continuity packets, the remote processor may contemporaneously generate the output file. For example, the remote computing device 124 may receive the second continuity packet first and the first continuity packet second, but not yet have received the end-of-file continuity packet; and after that, the remote processor 124 may order the continuity packets into an output order having the first continuity packet first and the second continuity packet second. In some embodiments, while the output file is being generated, the continuity packets are configured to be readable by external processes. Examples of such external processes include maintenance processes configured to check for device maintenance status or error messages. Such external process may be able to read and/or respond to maintenance requests or errors prior to ordering, such that an error message contained in the continuity packets can be read prior to completing the generation of the output file. For example, if a patient is undergoing a CT scan performed by a CT scanner, a processor may monitor and read the data in real-time or near real-time to detect an error message. In this example, if the CT scanner generates a continuity packet containing an error message indicating a fault with the CT scanner (e.g., the data obtained by the CT scanner will be unusable), then, at the direction of such an external monitoring process, the remote processor 124 may read the error message prior to ordering and generating the output file and stop the CT scanner during the CT scan. Stopping the CT scan prior to its completion would limit the patient's unnecessary exposure to X-rays, as any exposure after the error may not result in usable data.

At step 508, the method 500 may include, at the remote computing device, using the end tag to generate an end-of-file indicator. For example, a flag may be used or a variable may be set as an end-of-file indicator when the end-of-file continuity packet containing the end tag "ZZ" is received (i.e., the remote processor may change a variable "end-of-file-reached" from "false" to "true").

At step 510, the method 500 may include using the header information, the map packet, and the end-of-file indicator to determine whether any continuity packets remain to be received. For example, if the first continuity packet containing the first header information of "AA000000AA" and the end-of-file continuity packet containing the end-of-file header information "AA000002ZZ" (and thus the end tag "ZZ") have been received, the remote processor 124 may determine that the second continuity packet has not been received. If any continuity packets remain to be received, the method 500 proceeds to step 512. If all continuity packets have been received, the method 300 proceeds to step 520.

At step 512, if any continuity packets remain to be received, the method 500 may include determining a non-zero wait time period. For example, if the second continuity packet has not been received, the remote processor 124 may determine a wait time period. The wait time period may be between two seconds and ten seconds, or any other suitable period of time.

At step 514, the method 500 may include, at the remote computing device, determining if any continuity packets were received within the wait time period. For example, if the second continuity packet, which had not been previously received, is received within the wait time period, the remote computing device may determine that a continuity packet was received within the wait time period, subsequent to which the method 500 proceeds to step 516. However, if the second continuity packet is not received within the wait time period, the remote processor 124 may determine that the continuity packet was not received within the wait time period, subsequent to which the method 500 proceeds to step 518.

At step 516, responsive to receiving another continuity packet within the non-zero wait time period, the method 500 may include the remote computing device continuing to generate the output file. For example, if the determination is that the second continuity packet that had not been previously received is received within the wait time period, then the remote processor 124 may continue generating the output file. The method 500 may then return to step 520.

At step 518, responsive to determining the non-zero wait time period and not receiving another continuity packet within the non-zero wait time period, the method 500 may include the remote computing device transmitting an error signal. For example, if the determination is that the second continuity packet that had not been previously received was not received within the wait time period, the remote processor 124 may direct the remote network adapter 132 to transmit an error message and/or the remote output 130 to present the error message (e.g., "Error: Incomplete Data").

At step 520, responsive to determining that every continuity packet has been received, the method 500 includes transmitting the output file. For example, if the first continuity packet, the second continuity packet, and the end-of-file continuity packet have been received and ordered (e.g., into an output file), the remote processor 124 may direct the remote network adapter 132 to transmit the output file via the network 134.

FIGS. 3A, 3B, 4, 5A, and 5B are not intended to be limiting: the methods 300, 400, and 500 can include more or fewer steps and/or processes than those illustrated in FIGS. 3A, 3B, 4, 5A and 5B. Further, the order of the steps of the methods 300, 400, and 500 is not intended to be limiting; the steps can be arranged in any suitable order.

The term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying a set of instructions for execution by the machine and causing the machine to perform any one or more of the methodologies of the present disclosure. The term "computer-readable storage medium" shall accordingly be taken to include, but not be limited to, solid-state memories, optical media, and magnetic media.

Any of the systems and methods described in this disclosure may be used in connection with rehabilitation. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. The patient may prepare an area of his or her body for the surgical procedure by performing the one or more sets of exercises, thereby strengthening muscle groups, improving existing and/or establishing new muscle memory, enhancing mobility, improving blood flow, and/or the like.

In some embodiments, the systems and methods described herein may use artificial intelligence and/or machine learning to generate a prehabilitation treatment plan for a user. Additionally, or alternatively, the systems and methods described herein may use artificial intelligence and/or machine learning to recommend an optimal exercise machine configuration for a user. For example, a data model may be trained on historical data such that the data model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the patient, a recommended health professional specialist to contact, and/or the like.

Consistent with the above disclosure, the examples of systems and method enumerated in the following clauses are specifically contemplated and are intended as a non-limiting set of examples.

Clause 1. A system for transmitting data comprising:
an information-generating device;
a processor in communication with the information-generating device, wherein the processor is configured to:
receive data;
generate a map packet;
transmit the map packet;
using the data, generate continuity packets, wherein each of the continuity packets comprises a contiguous portion of the data;
transmit the continuity packets; and
using the map packet and the continuity packets, cause an output file to be generated.

Clause 2. The system of any clause herein, wherein the processor is further configured to:
cause a remote processor to receive the map packet;
cause the remote processor to receive the continuity packets; and
wherein, responsive to the remote processor receiving the map packet and at least two of the continuity packets, the remote processor generates the output file.

Clause 3. The system of any clause herein, wherein, as the continuity packets are received, the remote processor generates the output file in real-time or near real time.

Clause 4. The system of any clause herein, wherein the remote processor receives the continuity packets in an initial order; and
wherein, using the map packet, the processor is configured to cause the remote processor to generate the output file by ordering the continuity packets from the initial order into an output order.

Clause 5. The system of any clause herein, wherein one or more of the continuity packets comprise header information; and
wherein a contiguous portion of the map packet corresponds to a contiguous portion of the header information.

Clause 6. The system of any clause herein, wherein each of the continuity packets comprises header information.

Clause 7. The system of any clause herein, wherein the map packet comprises end-of-file information;
wherein one or more of the continuity packets comprise header information; and
wherein header information of an end-of-file continuity packet comprises an end tag corresponding to a contiguous portion of the end-of-file information.

Clause 8. The system of any clause herein, wherein the information-generating device comprises a medical device.

Clause 9. The system of any clause herein, wherein the medical device is an orthopedic rehabilitation device.

Clause 10. The system of any clause herein, further comprising a memory device operatively coupled to the processor, wherein the memory device stores instructions, and wherein the processor is configured to execute the instructions.

Clause 11. A method for operating an information-generating device, comprising:
receiving data;
generating a map packet;
transmitting the map packet;
using the data to generate continuity packets, wherein each of the continuity packets comprises a contiguous portion of the data;
transmitting the continuity packets; and using the map packet and the continuity packets to cause an output file to be generated.

Clause 12. The method of any clause herein, further comprising:

causing a remote processor to receive the map packet;

causing the remote processor to receive the continuity packets; and wherein, responsive to the remote processor receiving the map packet and at least two of the continuity packets, the remote processor generates the output file.

Clause 13. The method of any clause herein, wherein, as the continuity packets are received, the remote processor generates the output file in real-time or near real time.

Clause 14. The method of any clause herein, wherein the remote processor receives the continuity packets in an initial order; and wherein, using the map packet, the method further comprises causing the remote processor to generate the output file by ordering the continuity packets from the initial order into an output order.

Clause 15. The method of any clause herein, wherein one or more of the continuity packets comprise header information; and wherein a contiguous portion of the map packet corresponds to a contiguous portion of the header information.

Clause 16. The method of any clause herein, wherein each of the continuity packets comprises header information.

Clause 17. The method of any clause herein, wherein the map packet comprises end-of-file information;

wherein one or more of the continuity packets comprise header information; and wherein header information of an end-of-file continuity packet comprises an end tag corresponding to a contiguous portion of the end-of-file information.

Clause 18. The method of any clause herein, wherein the information-generating device comprises a medical device.

Clause 19. The method of any clause herein, wherein the medical device is an orthopedic rehabilitation device.

Clause 20. A tangible, non-transitory computer-readable storage medium storing instructions that, when executed, cause a processor to:

receive data from an information-generating device;

generate a map packet;

transmit the map packet;

using the data, generate continuity packets, wherein each of the continuity packets comprises a contiguous portion of the data;

transmit the continuity packets; and using the map packet and the continuity packets, cause an output file to be generated.

Clause 21. The tangible, non-transitory computer-readable storage medium of any clause herein, wherein the instructions further cause the processor to:

cause a remote processor to receive the map packet;

cause the remote processor to receive the continuity packets; and responsive to the remote processor receiving the map packet and at least two of the continuity packets, cause the remote processor to generate the output file.

Clause 22. The tangible, non-transitory computer-readable storage medium of any clause herein, wherein, as the continuity packets are received, the remote processor generates the output file.

Clause 23. The tangible, non-transitory computer-readable storage medium of any clause herein, wherein the remote processor receives the continuity packets in an initial order; and wherein, using the map packet, the instructions further cause the processor to cause the remote processor to generate the output file by ordering the continuity packets from the initial order into an output order.

Clause 24. The tangible, non-transitory computer-readable storage medium of any clause herein, wherein one or more of the continuity packets comprise header information; and wherein a contiguous portion of the map packet corresponds to a contiguous portion of the header information.

Clause 25. The tangible, non-transitory computer-readable storage medium of any clause herein, wherein each of the continuity packets comprises header information.

Clause 26. The tangible, non-transitory computer-readable storage medium of any clause herein wherein the map packet comprises end-of-file information;

wherein one or more of the continuity packets comprise header information; and wherein header information of an end-of-file continuity packet comprises an end tag corresponding to a contiguous portion of the end-of-file information.

Clause 27. The tangible, non-transitory computer-readable storage medium of any clause herein, wherein the information-generating device comprises a medical device.

Clause 28. The tangible, non-transitory computer-readable storage medium of any preceding clause, wherein the medical device is an orthopedic rehabilitation device.

Clause 29. A system for ordering of asynchronously transmitted data, comprising:

a processor configured to:

receive, from an information-generating device, a map packet;

receive, from the information-generating device, continuity packets in an initial order; and responsive to receiving the map packet and at least two of the continuity packets, use the map packet to generate an output file by ordering the continuity packets from the initial order into an output order.

Clause 30. The system of any clause herein, wherein, as the continuity packets are received, the processor is configured to generate the output file in real-time or near real time.

Clause 31. The system of any clause herein, wherein, while the output file is being generated, the continuity packets are configured to be readable by external processes.

Clause 32. The system of any clause herein, wherein one or more of the continuity packets comprise header information; and wherein a contiguous portion of the map packet corresponds to a contiguous portion of the header information.

Clause 33. The system of any clause herein, wherein each of the continuity packets comprises header information.

Clause 34. The system of any clause herein, wherein the map packet comprises end-of-file information;

wherein one or more of the continuity packets comprise header information; and wherein header information of an end-of-file continuity packet comprises an end tag corresponding to a contiguous portion of the end-of-file information.

Clause 35. The system of any clause herein, wherein, using the end tag, the processor is further configured to generate an end-of-file indication.

Clause 36. The system of any clause herein, wherein the processor is further configured to:

use the header information, the map packet, and the end-of-file indication, to determine whether any continuity packet remains to be received;

responsive to any continuity packets remaining to be received, determine a non-zero wait time period;

responsive to receiving another continuity packet within the non-zero wait time period, continue to generate the output file; and responsive to receiving no further continuity packets within the non-zero wait time period, transmit an error signal.

Clause 37. The system of any clause herein, wherein the processor is further configured to:

use the header information, the map packet, and the end-of-file indication to determine whether every continuity packet has been received; and if every continuity packet has been received, transmit the output file.

Clause 38. The system of any clause herein, wherein the information-generating device comprises a medical device.

Clause 39. The system of any clause herein, wherein the medical device is an orthopedic rehabilitation device.

Clause 40. The system of any clause herein, further comprising a memory device operatively coupled to the processor, wherein the memory device stores instructions, and wherein the processor is configured to execute the instructions.

Clause 41. A method for operating a computing device, comprising:

receiving, from an information-generating device, a map packet;

receiving, from the information-generating device, continuity packets in an initial order; and responsive to receiving the map packet and at least two of the continuity packets, using the map packet to generate an output file by ordering the continuity packets from the initial order into an output order.

Clause 42. The method of any clause herein, wherein, as the continuity packets are received, the output file is generated in real-time or near real-time.

Clause 43. The method of any clause herein, wherein, while the output file is being generated, the continuity packets are configured to be readable by external processes.

Clause 44. The method of any clause herein, wherein one or more of the continuity packets comprise header information; and wherein a contiguous portion of the map packet corresponds to a contiguous portion of the header information.

Clause 45. The method of any clause herein, wherein each of the continuity packets comprises header information.

Clause 46. The method of any clause herein, wherein the map packet comprises end-of-file information;

wherein one or more of the continuity packets comprise header information; and wherein header information of an end-of-file continuity packet comprises an end tag corresponding to a contiguous portion of the end-of-file information.

Clause 47. The method of any clause herein, further comprising using the end tag to generate an end-of-file indication.

Clause 48. The method of any clause herein, further comprising:

using the header information, the map packet, and the end-of-file indication to determine whether every continuity packet has been received;

responsive to any continuity packets remaining to be received, determining a non-zero wait time period;

responsive to receiving another continuity packet within the non-zero wait time period, continuing to generate the output file; and responsive to receiving no further continuity packets within the non-zero wait time period, transmitting an error signal.

Clause 49. The method of any clause herein, further comprising:

using the header information, the map packet, and the end-of-file indication to determine whether every continuity packet has been received; and if every continuity packet has been received, transmitting the output file.

Clause 50. The method of any clause herein, wherein the information-generating device comprises a medical device.

Clause 51. The method of any clause herein, wherein the medical device is an orthopedic rehabilitation device.

Clause 52. A tangible, non-transitory computer-readable storage medium storing instructions that, when executed, cause a processor to:

receive, from an information-generating device, a map packet;

receive, from the information-generating device, continuity packets in an initial order; and responsive to receiving the map packet and at least two of the continuity packets, using the map packet to generate an output file by ordering the continuity packets from the initial order into an output order.

Clause 53. The tangible, non-transitory computer-readable storage medium of any clause herein, wherein, as the continuity packets are received, the processor contemporaneously generates the output file.

Clause 54. The tangible, non-transitory computer-readable storage medium of any clause herein, wherein the continuity packets are configured to be readable by external processes while the output file is being generated.

Clause 55. The tangible, non-transitory computer-readable storage medium of any clause herein, wherein one or more of the continuity packets comprise header information; and wherein a contiguous portion of the map packet corresponds to a contiguous portion of the header information.

Clause 56. The tangible, non-transitory computer-readable storage medium of any clause herein, wherein each of the continuity packets comprises header information.

Clause 57. The tangible, non-transitory computer-readable storage medium of any clause herein, wherein the map packet comprises end-of-file information;

wherein one or more of the continuity packets comprise header information; and wherein header information of an end-of-file continuity packet comprises an end tag corresponding to a contiguous portion of the end-of-file information.

Clause 58. The tangible, non-transitory computer-readable storage medium of any preceding clause, wherein the instructions further cause the processor to use the end tag to generate an end-of-file indication.

Clause 59. The tangible, non-transitory computer-readable storage medium of any clause herein, wherein the instructions further cause the processor to:

use the header information, the map packet, and the end-of-file indication, to determine whether any continuity packet remains to be received;

responsive to any continuity packet remaining to be received, determine a non-zero wait time period;

responsive to receiving another continuity packet within the non-zero wait time period, continue generating the output file; and responsive to receiving no further continuity packets within the non-zero wait time period, transmit an error signal.

Clause 60. The tangible, non-transitory computer-readable storage medium of any clause herein, wherein the instructions further cause the processor to:

use the header information, the map packet, and the end-of-file indication to determine whether every continuity packet has been received; and responsive to determining that every continuity packet has been received, transmit the output file.

Clause 61. The tangible, non-transitory computer-readable storage medium of any clause herein, wherein the information-generating device comprises a medical device.

Clause 62. The tangible, non-transitory computer-readable storage medium of any preceding clause, wherein the medical device is an orthopedic rehabilitation device.

Clause 63. A system for transmitting data and ordering asynchronous data, comprising:

an information-generating device comprising a device-side processor configured to:
 receive data;
 generate a map packet;
 transmit the map packet;
 use the data to generate continuity packets, wherein each of the continuity packets comprises a contiguous portion of the data;
 transmit the continuity packets; and a remote computing device comprising a remote processor configured to:
 receive, from the information-generating device, the map packet;
 receive, from the information-generating device, the continuity packets in an initial order; and
 responsive to receiving at least two of the continuity packets and the map packet, use the map packet to generate an output file by ordering the continuity packets from the initial order into an output order.

Clause 64. The system of any clause herein, wherein, as the remote processor receives the continuity packets, the remote processor contemporaneously generates the output file.

Clause 65. The system of any clause herein, wherein, while the output file is being generated, the continuity packets are configured to be readable by external processes.

Clause 66. The system of any clause herein, wherein one or more of the continuity packets comprise header information; and wherein a contiguous portion of the map packet corresponds to a contiguous portion of the header information.

Clause 67. The system of any clause herein, wherein each of the continuity packets comprises header information.

Clause 68. The system of any clause herein, wherein the map packet comprises end-of-file information;

wherein one or more of the continuity packets comprise header information; and wherein header information of an end-of-file continuity packet comprises an end tag corresponding to a contiguous portion of the end-of-file information.

Clause 69. The system of any clause herein, wherein the remote processor is further configured to, using the end tag, generate an end-of-file indication.

Clause 70. The system of any clause herein, wherein the remote processor is further configured to:

use the header information, the map packet, and the end-of-file indication to determine whether any continuity packets remain to be received;

if any continuity packets remain to be received, determine a non-zero wait time period;

responsive to determining the non-zero wait time period and receiving another continuity packet within the non-zero wait time period, continue generating the output file; and responsive to determining the non-zero wait time period and not receiving another continuity packet within the non-zero wait time period, transmit an error signal.

Clause 71. The system of any clause herein, wherein the remote processor is further configured to:

use the header information, the map packet, and the end-of-file indication to determine whether every continuity packet has been received; and responsive to determining that every continuity packet has been received, transmit the output file.

Clause 72. The system of any clause herein, wherein the information-generating device comprises a medical device.

Clause 73. The system of any clause herein, wherein the medical device is an orthopedic rehabilitation device.

Clause 74. The system of any clause herein, further comprising a device-side memory device operatively coupled to the device-side processor, wherein the device-side memory device stores device-side instructions, and wherein the device-side processor is configured to execute the device-side instructions.

Clause 75. The system of any clause herein, further comprising a remote memory device operatively coupled to the remote processor, wherein the remote memory device stores remote instructions, and wherein the remote processor is configured to execute the remote instructions.

Clause 76. A computer-implemented system, comprising:

an electromechanical device configured to be manipulated by a patient while performing an exercise session;

a processor in communication with the electromechanical device, wherein the processor is configured to:
 receive data;
 generate a map packet;
 transmit the map packet;
 using the data, generate continuity packets, wherein each of the continuity packets comprises a contiguous portion of the data;
 transmit the continuity packets; and
 using the map packet and the continuity packets, cause an output file to be generated.

Clause 77. The computer-implemented system of any clause herein, wherein the processor is further configured to:

cause a remote processor to receive the map packet;

cause the remote processor to receive the continuity packets; and wherein, responsive to the remote processor receiving the map packet and at least two of the continuity packets, the remote processor generates the output file.

Clause 78. The computer-implemented system of any clause herein, wherein, as the continuity packets are received, the remote processor generates the output file in real-time or near real time.

No part of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A computer-implemented system, comprising:
an electromechanical device configured to be manipulated by a patient while the patient performs an exercise session;
a first processor in communication with the electromechanical device, wherein the first processor is configured to:
receive data;
generate a map packet;
transmit the map packet;
using the data, generate continuity packets, wherein each of the continuity packets comprises a contiguous portion of the data;
transmit the continuity packets;
using the map packet and the continuity packets, cause an output file to be generated, by:
causing a second processor to receive the map packet; and
causing the second processor to receive the continuity packets, wherein:
responsive to the second processor receiving the map packet and at least two of the continuity packets, the second processor generates the output file in real-time or near real time,
the second processor receives the continuity packets in an initial order, and
using the map packet, the first processor is configured to cause the second processor to generate the output file by ordering the continuity packets from the initial order into an output order.

2. The system of claim 1, wherein the information-generating device comprises a medical device.

3. The system of claim 2, wherein the medical device is an orthopedic rehabilitation device.

4. A system for transmitting data comprising:
an information-generating device;
a first processor in communication with the information-generating device, wherein the first processor is configured to:
receive data;
generate a map packet;
transmit the map packet;
using the data, generate continuity packets, wherein each of the continuity packets comprises a contiguous portion of the data;
transmit the continuity packets;
using the map packet and the continuity packets, cause an output file to be generated, by:
causing a second processor to receive the map packet; and
causing the second processor to receive the continuity packets, wherein:
responsive to the second processor receiving the map packet and at least two of the continuity packets, the second processor generates the output file in real-time or near real time,
the second processor receives the continuity packets in an initial order, and
using the map packet, the first processor is configured to cause the second processor to generate the output file by ordering the continuity packets from the initial order into an output order.

5. The system of claim 4, wherein one or more of the continuity packets comprise header information; and
wherein a contiguous portion of the map packet corresponds to a contiguous portion of the header information.

6. The system of claim 4, wherein each of the continuity packets comprises header information.

7. The system of claim 4, wherein the map packet comprises end-of-file information;
wherein one or more of the continuity packets comprise header information; and
wherein header information of an end-of-file continuity packet comprises an end tag corresponding to a contiguous portion of the end-of-file information.

8. The system of claim 4, further comprising a memory device operatively coupled to the first processor, wherein the memory device stores instructions, and wherein the first processor is configured to execute the instructions.

9. A method for operating an information-generating device, comprising:
receiving data;
generating a map packet;
transmitting the map packet;
using the data to generate continuity packets, wherein each of the continuity packets comprises a contiguous portion of the data;
transmit the continuity packets;
using the map packet and the continuity packets to cause an output file to be generated by:
causing a second processor to receive the map packet; and
causing the second processor to receive the continuity packets, wherein:
responsive to the second processor receiving the map packet and at least two of the continuity packets, the second processor generates the output file in real-time or near real time,
the second processor receives the continuity packets in an initial order, and
using the map packet, a first processor is configured to cause the second processor to generate the output file by ordering the continuity packets from the initial order into an output order.

10. The method of claim 9, wherein each of the continuity packets comprises header information.

11. The method of claim 9, wherein one or more of the continuity packets comprise header information; and
wherein a contiguous portion of the map packet corresponds to a contiguous portion of the header information.

12. The method of claim 9, wherein the map packet comprises end-of-file information;
wherein one or more of the continuity packets comprise header information; and wherein header information of an end-of-file continuity packet comprises an end tag corresponding to a contiguous portion of the end-of-file information.

13. The method of claim 9, wherein the information-generating device comprises a medical device.

14. The method of claim 13, wherein the medical device is an orthopedic rehabilitation device.

15. A tangible, non-transitory computer-readable storage medium storing instructions that, when executed, cause a first processor to:
receive data from an information-generating device;
generate a map packet;
transmit the map packet;
using the data, generate continuity packets, wherein each of the continuity packets comprises a contiguous portion of the data;
transmit the continuity packets;
using the map packet and the continuity packets, cause an output file to be generated, by:
causing a second processor to receive the map packet;
causing the second processor to receive the continuity packets, wherein:
responsive to the second processor receiving the map packet and at least two of the continuity packets, the second processor generates the output file in real-time or near real time,
the second processor receives the continuity packets in an initial order, and
using the map packet, the first processor is configured to cause the second processor to generate the output file.

16. The tangible, non-transitory computer-readable storage medium of claim 15, wherein one or more of the continuity packets comprise header information; and
wherein a contiguous portion of the map packet corresponds to a contiguous portion of the header information.

17. The tangible, non-transitory computer-readable storage medium of claim 15, wherein each of the continuity packets comprises header information.

18. The tangible, non-transitory computer-readable storage medium of claim 15 wherein the map packet comprises end-of-file information;
wherein one or more of the continuity packets comprise header information; and
wherein header information of an end-of-file continuity packet comprises an end tag corresponding to a contiguous portion of the end-of-file information.

19. The tangible, non-transitory computer-readable storage medium of claim 15, wherein the information-generating device comprises a medical device.

* * * * *